United States Patent [19]

Sreekrishna et al.

[11] Patent Number: 5,002,876
[45] Date of Patent: Mar. 26, 1991

[54] YEAST PRODUCTION OF HUMAN TUMOR NECROSIS FACTOR

[75] Inventors: Kotikanyadan Sreekrishna, Bartlesville; Motohiro Fuke, Tulsa; Rica H. Potenz, Bartlesville, all of Okla.

[73] Assignee: Phillips Petroleum Company, Bartlesville, Okla.

[21] Appl. No.: 909,528

[22] Filed: Sep. 22, 1986

[51] Int. Cl.$^5$ .................... C12P 21/00; C12P 21/02; C12N 15/00

[52] U.S. Cl. ................... 435/69.5; 435/320.1; 435/251; 435/255; 435/256; 435/172.3; 935/37; 935/56; 935/69; 536/27

[58] Field of Search ............ 435/68, 70, 91, 172.3, 435/255, 256, 320; 536/27; 935/28, 37, 56, 69

[56] References Cited

U.S. PATENT DOCUMENTS

| | | | |
|---|---|---|---|
| 4,599,311 | 7/1986 | Kawasaki | 435/71 |
| 4,677,063 | 6/1987 | Mark et al. | 435/68 |
| 4,677,064 | 6/1987 | Mark et al. | 435/68 |

FOREIGN PATENT DOCUMENTS

| | | | |
|---|---|---|---|
| 0123544 | 10/1984 | European Pat. Off. | 435/68 |
| 0123811 | 11/1984 | European Pat. Off. | 435/68 |
| 0166996 | 1/1986 | European Pat. Off. | 435/68 |
| 0168214 | 1/1986 | European Pat. Off. | 435/68 |
| 0183071 | 6/1986 | European Pat. Off. | 435/68 |

OTHER PUBLICATIONS

Ellis et al, *Mol. Cell. Biol.,* May 1985, pp. 1111–1121, vol. 5(5), "Isolation of alcohol oxidase and two other".
Cregg et al, *Mol. Cell. Biol.,* Dec. 1985, pp. 3376–3385, vol. 5(12), "Pichia pastoris as a host for transformations".
Scherer et al, *Proc. Natl. Acad. Sci.,* vol. 76, pp. 3576.
Journal of Biotechnology, vol. 3, pp. 141–153.
Nature, vol. 318, pp. 665–667.
Proc. Natl. Acad. Sci. U.S.A., vol. 82, pp. 5756–5760.
J. Exp. Med., vol. 162, pp. 1099–1104.
Journal of Biological Chemistry, vol. 260, pp. 12,214–12,218.
Proc. Natl. Acad. Sci. U.S.A., vol. 82, pp. 6637–6641.
Science, vol. 230, pp. 943–945.
Jpn. J. Cancer Res., vol. 76, pp. 631–636.
Jpn. J. Cancer Res., vol. 76, pp. 395–399.
Journal of Immunology, vol. 135, pp. 2492–2497.
JNCI, vol. 74, pp. 1255–1260.
Int. J. Cancer, vol. 36, pp. 69–73.
Journal of Immunology, vol. 135, pp. 3962–3968.
J. Exp. Med., vol. 162, pp. 1512–1530.
Genetic Technology News, Nov. 1985.
Cancer Immunol. Immunother., vol. 20, pp. 1–5 (1985).
Science, vol. 229, pp. 869–871 (1985).
Journal of Biological Chemistry, vol. 260, pp. 2345–2354 (1985).
Nucleic Acids Research, vol. 13, pp. 6361–6373 (1985).
Science, vol. 230, pp. 630–632 (1985).
Journal of Immunology, vol. 135, pp. 2069–2073.
Proc. Natl. Acad. Sci., U.S.A., vol. 83, pp. 446–450.
Nature, vol. 312, pp. 724–729 (1984).
Proc. Natl. Acad. Sci., U.S.A., vol. 82, pp. 6960–6064.
Int. J. Cancer, vol. 36, pp. 395–400.
Nature, vol. 313, pp. 803–806.
Eur. J. Biochem., vol. 152, pp. 515–522.

*Primary Examiner*—Robin L. Teskin
*Attorney, Agent, or Firm*—J. E. Phillips

[57] ABSTRACT

Novel DNA constructs comprising yeast regulatory regions plus the structural coding region for human tumor necrosis factor, are disclosed. These novel constructs are incorporated into a variety of linear and circular plasmids. Such plasmids are used for yeast transformation and ultimately for the production of human tumor necrosis factor by yeast.

7 Claims, 9 Drawing Sheets

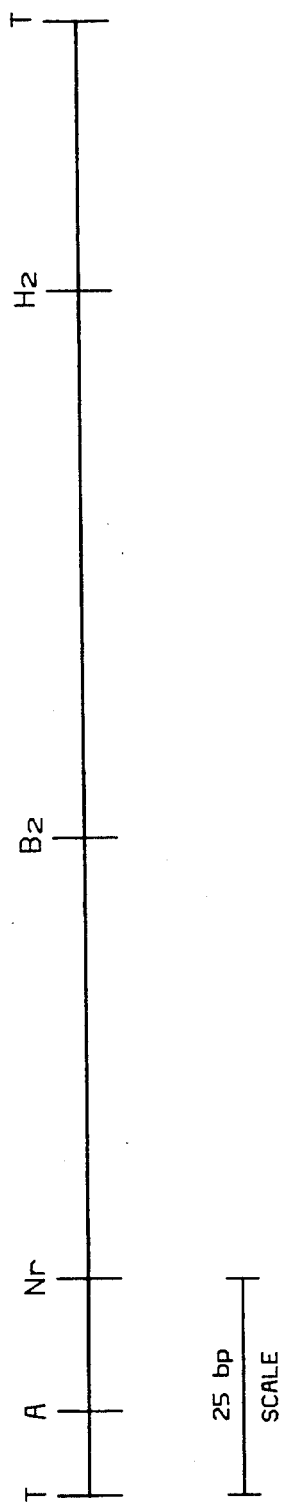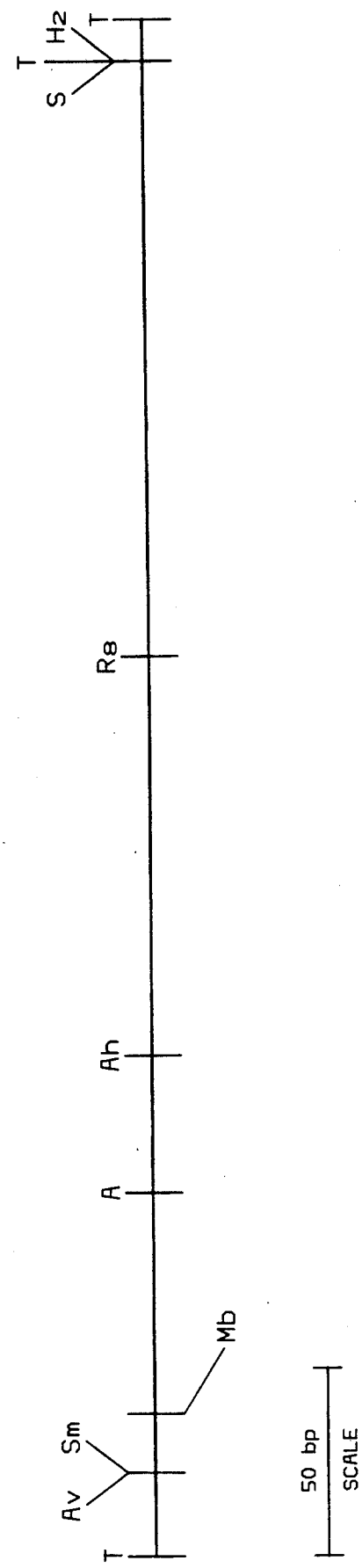
FIG. 11
FIG. 12

YEAST PRODUCTION OF HUMAN TUMOR NECROSIS FACTOR

This invention relates to the use of recombinant DNA technology for the production of human tumor necrosis factor. In one aspect, the present invention relates to the expression of human tumor necrosis factor by yeast. In another aspect, the present invention relates to novel DNA constructs encoding human tumor necrosis factor. In yet another aspect, the present invention relates to novel organisms transformed with the above-described DNA constructs.

BACKGROUND

As recombinant DNA technology has developed in recent years, the controlled production by microorganisms of an enormous variety of useful polypeptides has become possible. Many eukaryotic polypeptides have already been produced by microorganisms and approved by the Food and Drug Administration for pharmeceutical applications, such as for example, human growth hormone, leukocyte interferons, human insulin and human proinsulin. The continued application of techniques already in hand is expected in the future to permit production by microorganisms of a variety of other useful polypeptide products. One such useful polypeptide product is human tumor necrosis factor.

Tumor necrosis factor (TNF) is an antitumor substance found in the sera of animals that have been treated with microbial products in two orderly events. The first event is a priming event that causes the activation and proliferation of macrophages and is associated with expansion of reticuloendothelial elements in the liver and spleen. For this priming event, mycobacteria such as Bacillus Calmette Guerin (BCG), corynebacteria such as *Corynebacterium parvum* and zymosan (yeast cell walls) are effective. The second event is an elicitation event which is necessary for appearance of TNF in the blood. This requires subsequent treatment of primed animals with lipopolysaccharide (LPS—a major constituent of the cell wall of gram-negative bacteria, also known as endotoxin or bacterial pyrogen). Using these principles, one can obtain sera with similar antitumor and cytotoxic properties from mice, rats and rabbits.

The cellular origin of TNF is macrophages (monocytes), thus TNF is also referred to as a monokine. TNF causes haemorrhagic necrosis and sometimes complete regression of certain tumors transplanted in mice and shows cytotoxic activity against certain tumor cell lines, but not against normal cells. TNF is not species specific, for example, mouse TNF is effective against a wide range of cell lines derived from human cancers.

The gene coding for human TNF has been cloned and expressed in *E. coli*. Human TNF appears to be encoded by a single copy gene. Four exons code for a precursor product of 233 amino acids and a mature product of 157 amino acids after an unusually long leader sequence has been removed. The molecular weight of human TNF is 45,000 daltons by gel filtration, and, as determined by SDS-PAGE, has a minimum molecular weight of 17,000. TNF has an isoelectric point of 5.6, does not have N-glycosylation sites and has only one possible S-S bridge. Mouse TNF also has been recently cloned and shows approximately 80% homology to human TNF at the (deduced) amino acid level. These recombinant TNF products have biological activities similar to that predicted from work with nonrecombinant TNF.

Recent evidence indicates that TNF belongs to a family of molecules having similar biological activities and varying degrees of sequence homologies. TNF is related in its cytotoxic activity to lymphotoxin. Both of these proteins exhibit synergism with interferon-γ in eliciting cytotoxic activity. TNF shares 30% amino acid homology with lymphotoxin. The single copy genes which encode these proteins share several structural features; each gene is approximately 3 kbp in length and is interrupted by three introns. In addition, these genes are closely linked and both have been mapped to human chromosome 6. In view of these similarities in biological activity, TNF is designated as TNF-α and lymphotoxin as TNF-β. Although their biological activities are similar, they are derived from different cell types and have distinct induction kinetics. TNF-α is secreted from monocytes 4–24 hours after induction, while TNF-β is secreted from T-lymphocytes 24–48 hours following induction. Unlike TNF-α, (molecular weight 17,000), TNF-β is a glycosylated protein of monomer molecular weight 25,000. TNF-α and TNF-β together appear to be the major cytolytic factors produced by peripheral blood leukocytes (PBL). Several lines of evidence suggest that TNF-α is identical to cachectin, which is one of the principle mediators of the lethal effect of LPS and which is assayed by its ability to suppress the activity of lipoprotein lipase in cultured adipocytes.

In view of the several useful biological activities of TNF with potential commercial value, a method for the production of human TNF-α with both yields and biological activities superior to that produced in *E. coli* would be highly desirable.

OBJECTS OF THE INVENTION

An object of the present invention, therefore, is a method for the production of human tumor necrosis factor in yeast.

Another object of the present invention is the preparation of novel DNA constructs which are capable of expressing human tumor necrosis factor in yeast at high levels.

These and other objects of the present invention will become apparant from inspection of the disclosure and claims herein provided.

STATEMENT OF THE INVENTION

In accordance with the present invention, we have discovered that human tumor necrosis factor can be produced by yeast in high yields by culturing yeast cells transformed with DNA constructs comprising human tumor necrosis factor coding regions under the control of yeast regulatory regions. A particular advantage of the production method of the present invention is the ease with which the method can be scaled up for large-scale production of tumor necrosis factor.

BRIEF DESCRIPTION OF THE FIGURES

FIG. 11 is a restriction map of a *Pichia pastoris* autonomous replication sequence (PARS1).

FIG. 12 is a restriction map of another *Pichia pastoris* autonomous replication sequence (PARS2).

Figure 1:
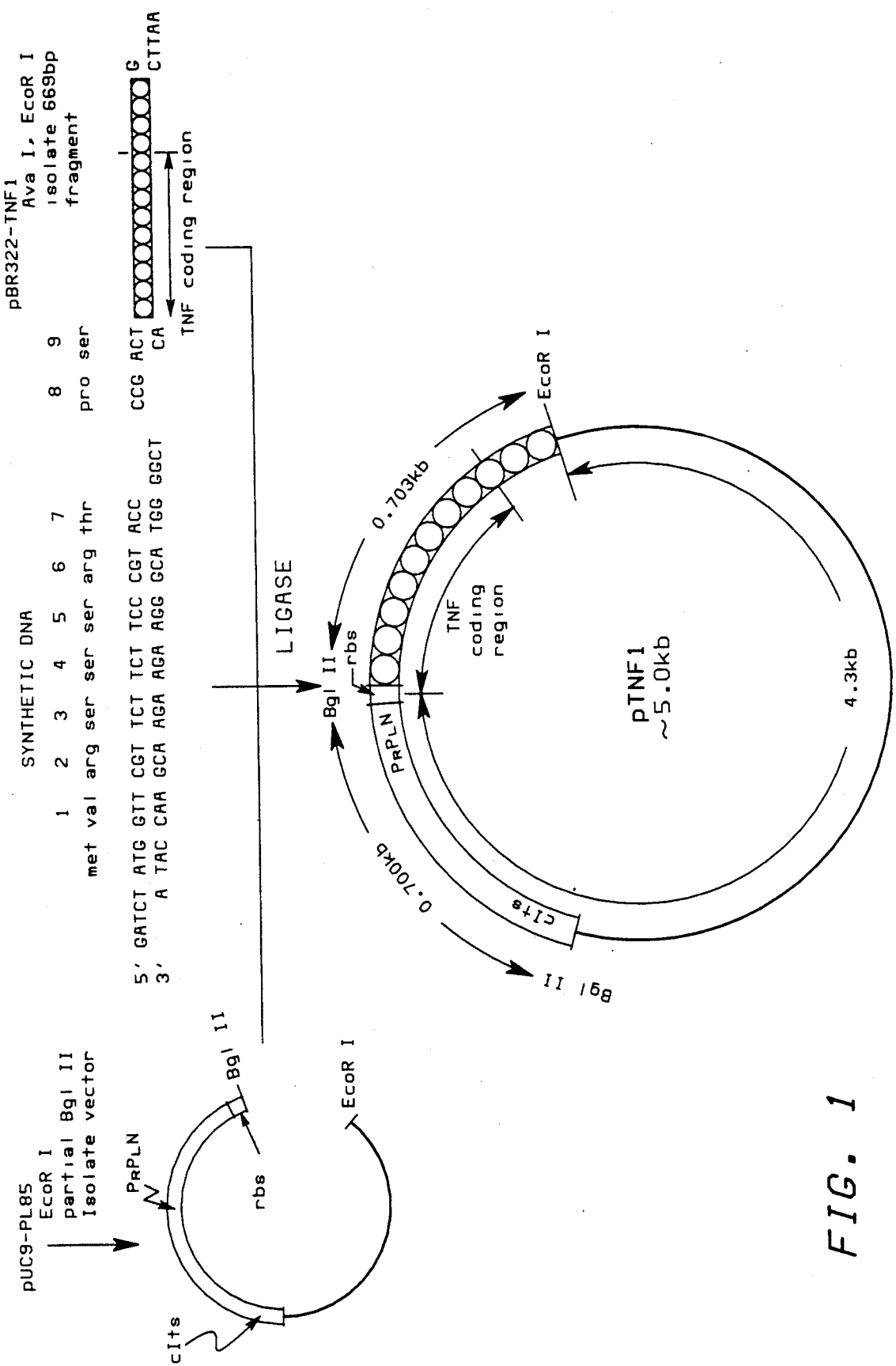
FIG. 1 is a diagram representing the essential components of plasmid pTNF1, including the location of major restriction sites and also including detail on the preparation of pTNF1 from pUC9-PL85 and pBR322-TNF1.

The following abbreviations are used in the text and in the Figures for the restriction enzymes:

| Abbreviation | Restriction Enzyme |
| --- | --- |
| A | AsuII |
| Ac | AccI |
| Ah | AhaIII |
| $Av_1$ | AvaI |
| $Av_2$ | AvaII |
| B | BamHI |
| $B_1$ | BglI |
| $B_2$ | BglII |
| Bc | BclI |
| Bl | BalI |
| Bn | BanI |
| Bs | BstEII |
| C | ClaI |
| F | FokI |
| H | HaeII |
| $H_2$ | HincII |
| $H_3$ | HindIII |
| Hh | HhaI |
| Hp | HpaII |
| K | KpnI |
| Mb | MboII |
| Na | NarI |
| Nc | NciI |
| $Nd_1$ | NdeI |
| Nr | NruI |
| Ps | PstI |
| $Pv_1$ | PvuI |
| $Pv_2$ | PvuII |
| $R_1$ | EcoRI |
| $R_5$ | EcoRV |
| S | SalI |
| Ss | SstI |
| St | StuI |
| T | TaqI |

DETAILED DESCRIPTION OF THE INVENTION

In accordance with the present invention, there is provided a novel DNA fragment comprising a yeast regulatory region and a polypeptide coding region wherein the polypeptide coding region codes for human tumor necrosis factor or portion s thereof, and wherein the yeast regulatory region is capable of controlling the transcription of messenger RNA when positioned at the 5'-end of the human tumor necrosis factor encoding region. Optionally, the novel DNA fragments of the present invention can also include a 3'-end sequence of DNA downstream of the polypeptide coding region, wherein the 3'-end sequence of DNA is capable of controlling the polyadenylation and termination of transcription of messenger RNA coded for by the polypeptide coding region. The combination of regulatory region, human tumor necrosis factor gene, and the transcriptional terminator fragment is referred to hereinafter as an expression cassette or expression unit.

Further in accordance with the present invention, there are provided novel linear and circular plasmids containing the above-described expression cassettes.

Still further in accordance with the present invention, there are provided essentially pure cultures of yeast strains transformed with the above-described linear or circular plasmids.

In accordance with yet another embodiment of the present invention, a process for preparing human tumor necrosis factor is described which comprises cultivating a yeast strain transformed with the above-described plasmids under conditions where expression of the desired protein product is obtained.

The gene coding for human tumor necrosis factor has been cloned and expressed in *E. coli*. Two general strategies have been utilized for such cloning. In the first strategy, tumor necrosis factor cDNA was isolated from mRNA from the HL-60 cell line using a synthetic oligonucleotide probe designed based on the amino acid sequence of tumor necrosis factor produced by the HL-60 cell line. The other cloning strategy employed involved the use of rabbit or murine tumor necrosis factor cDNA as a probe of a human genomic library. As a result of such work, numerous publications have appeared which provide large amounts of detail as to the nucelotide sequences of tumor necrosis factor coding regions and the amino acid sequences of various forms of the polypeptide.

As employed in this specification, the term "tumor necrosis factor" is intended to encompass all proteins, both naturally occurring and synthetic, which possess the antitumor properties observed of naturally occurring TNF molecules. Thus, TNF from a variety of natural sources as well as analogs and derivatives thereof are contemplated to be within the scope of the present invention. Many such TNF moieties are encoded by the nucleotide sequence set forth in restriction map 1:

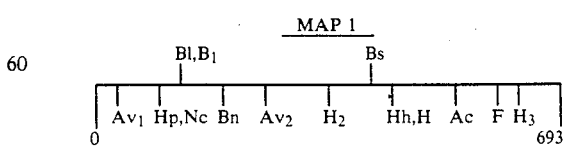

The specific TNF-encoding nucleotide sequence employed in the experimental work described in this specification is a 693 base pair $B_2$-$R_1$ fragment having the sequence set forth below as Sequence A:

| Sequence A | | | | | | | | | | | |
|---|---|---|---|---|---|---|---|---|---|---|---|
| 5'- ATG | GTT | CGT | TCT | TCT | TCC | CGT | ACC | CCG | AGT | GAC | AAG |
| CCT | GTA | GCC | CAT | GTT | GTA | GCA | AAC | CCT | CAA | GCT | GAG |
| GGG | CAG | CTC | CAG | TGG | CTG | AAC | CGC | CGG | GCC | AAT | GCC |
| CTC | CTG | GCC | AAT | GGC | GTG | GAG | CTG | AGA | GAT | AAC | CAG |
| CTG | GTG | GTG | CCA | TCA | GAG | GGC | CTG | TAC | CTC | ATC | TAC |
| TCC | CAG | GTC | CTC | TTC | AAG | GGC | CAA | GGC | TGC | CCC | TCC |
| ACC | CAT | GTG | CTC | CTC | ACC | CAC | ACC | ATC | AGC | CGC | ATC |
| GCC | GTC | TCC | TAC | CAG | ACC | AAG | GTC | AAC | CTC | CTC | TCT |
| GCC | ATC | AAG | AGC | CCC | TGC | CAG | AGG | GAG | ACC | CCA | GAG |
| GGG | GCT | GAG | GCC | AAG | CCC | TGG | TAT | GAG | CCC | ATC | TAT |
| CTG | GGA | GGG | GTC | TTC | CAG | CTG | GAG | AAG | GGT | GAC | CGA |
| CTC | AGC | GCT | GAG | ATC | AAT | CGG | CCC | GAC | TAT | CTC | GAC |
| TTT | GCC | GAG | TCT | GGG | CAG | GTC | TAC | TTT | GGG | ATC | ATT |
| GCC | CTG | TGA | GGAGGACGAA | | CATCCAACCT | | | TCCCAAACGC | | | |
| CTCCCCTGCC | | | CCAATCCCTT | | TATTACCCCC | | | TCCTTCAGAC | | | |
| ACCCTCAACC | | | TCTTCTGGCT | | CAAAAAGAGA | | | ATTGGGGGCT | | | |
| TAGGGTCGGA | | | ACCCAAGCTT | | AGAACTTTAA | | | GCAACAAGAC | | | |
| CACCACTTCG | | | AAACCTGGGA | | TTCAGGAATG | | | TGTGGCCTGC | | | |
| ACAGTGAAGT | | | GCTGGCAACC | | ACTAAG-3'. | | | | | | |

THis $B_2-R_1$ fragment encoding human tumor necrosis factor was incorporated into *Pichia pastoris* expression vectors as follows.

Figure 2:
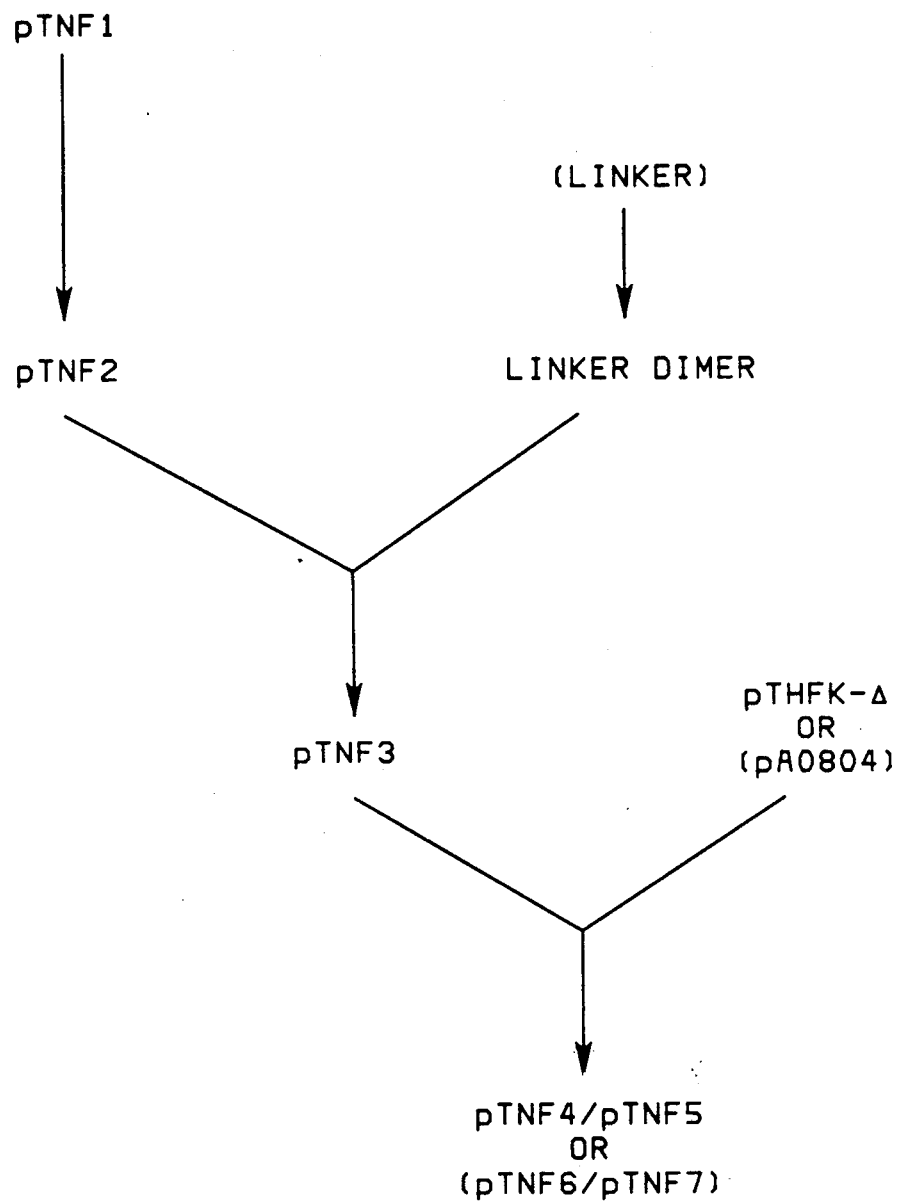
FIG. 2 is a schematic representation of the steps employed to prepare plasmids pTNF4/pTNF5 and pTNF6/pTNF7.

Plasmid pTNF1, containing the tumor necrosis factor gene described by Berent et al, DNA, Vol. 5, page 83 (1986) and derived as shown in FIG. 1 was employed as the source of the TNF gene for this work. The plasmid pTNF1 was converted into the yeast-based plasmids pTNF4, pTNF5, pTNF6 and pTNF7 as summarized in FIG. 2 and described in more detail below,. FIrst, plasmid pTNF1 was digested with $B_2$ to obtain two linear DNA fragments. The larger fragment obtained from pTNF1 contained both the TNF gene and also the ori and bla functions. This larger $B_2$ fragment was allowed to ligate back with itself producing the intermediate plasmid designated pTNF2. After amplication, plasmid pTNF2 was cleaved with $B_2$, and dimer of the B-Av linker (sequence shown as Sequence B) was inserted into the $B_2$ site of pTNF2.

SEQUENCE B

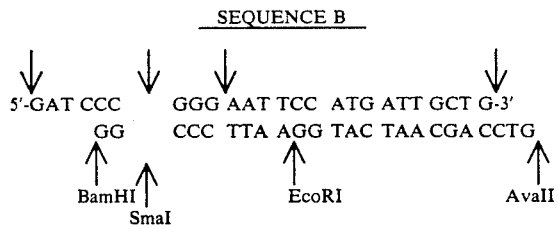

The above-described linker and pTNF2 linearized with $B_2$ are compatible because the restriction enzymes B and $B_2$ have an identical four necleotide sequence at the middle of their recognition sites. Convenient for further manipulation is the fact that the B-Av synthetic linker set forth in Sequence B also contains an internal $R_1$ site.

The ligated DNA resulting from combining pTNF2 which was linearized with $B_2$ and the linker set forth in Sequence A was used to transform an *E. coli* host. The plasmid DNA from several ampicillin resistant transformants was analyzed by digesting with $R_1$ to determine which plasmids had incorporated the synthetic linker represented in Sequence B, and thus were identified as the desired plasmid pTNF3.

Figure 5:
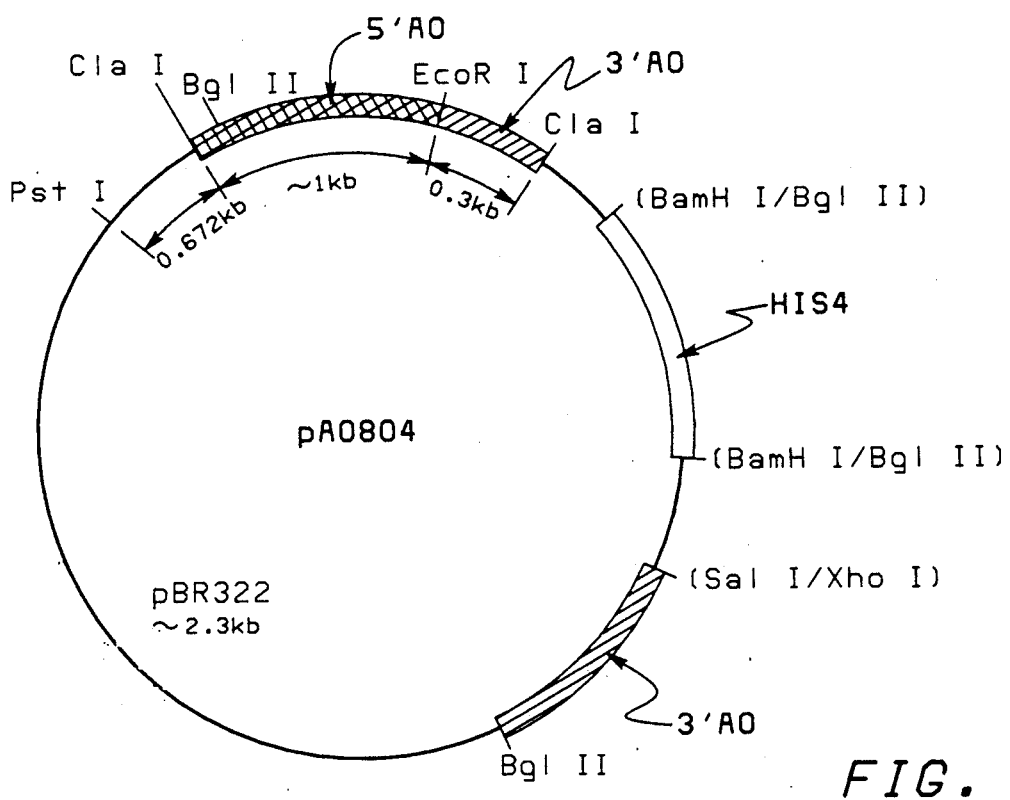
FIG. 5 is a diagram representing the essential components of plasmid pA0804, including the location of major restriction sites.
Figure 6:
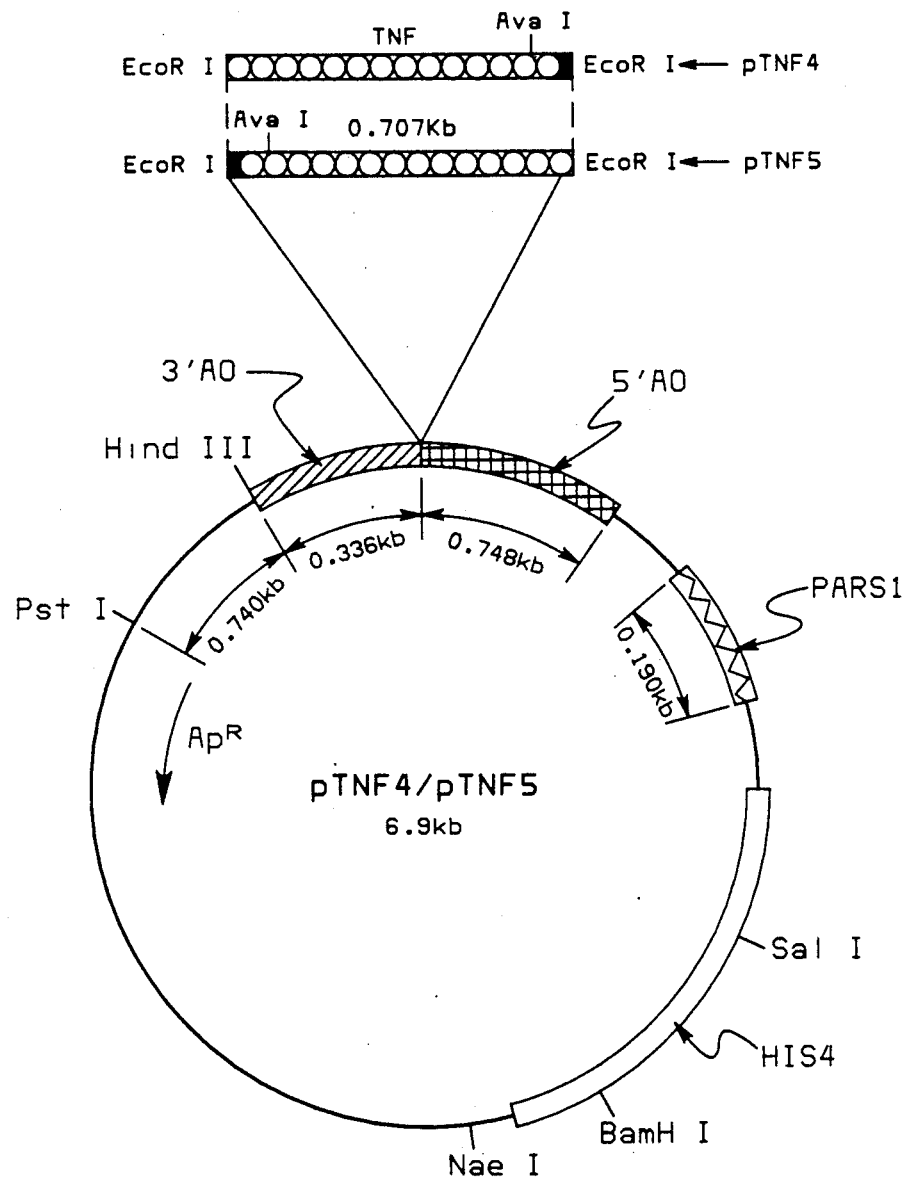
FIG. 6 is a diagram representing the essential components of plasmids pTNF4/pTNF5, including the location of major restriction sites.
Figure 7:
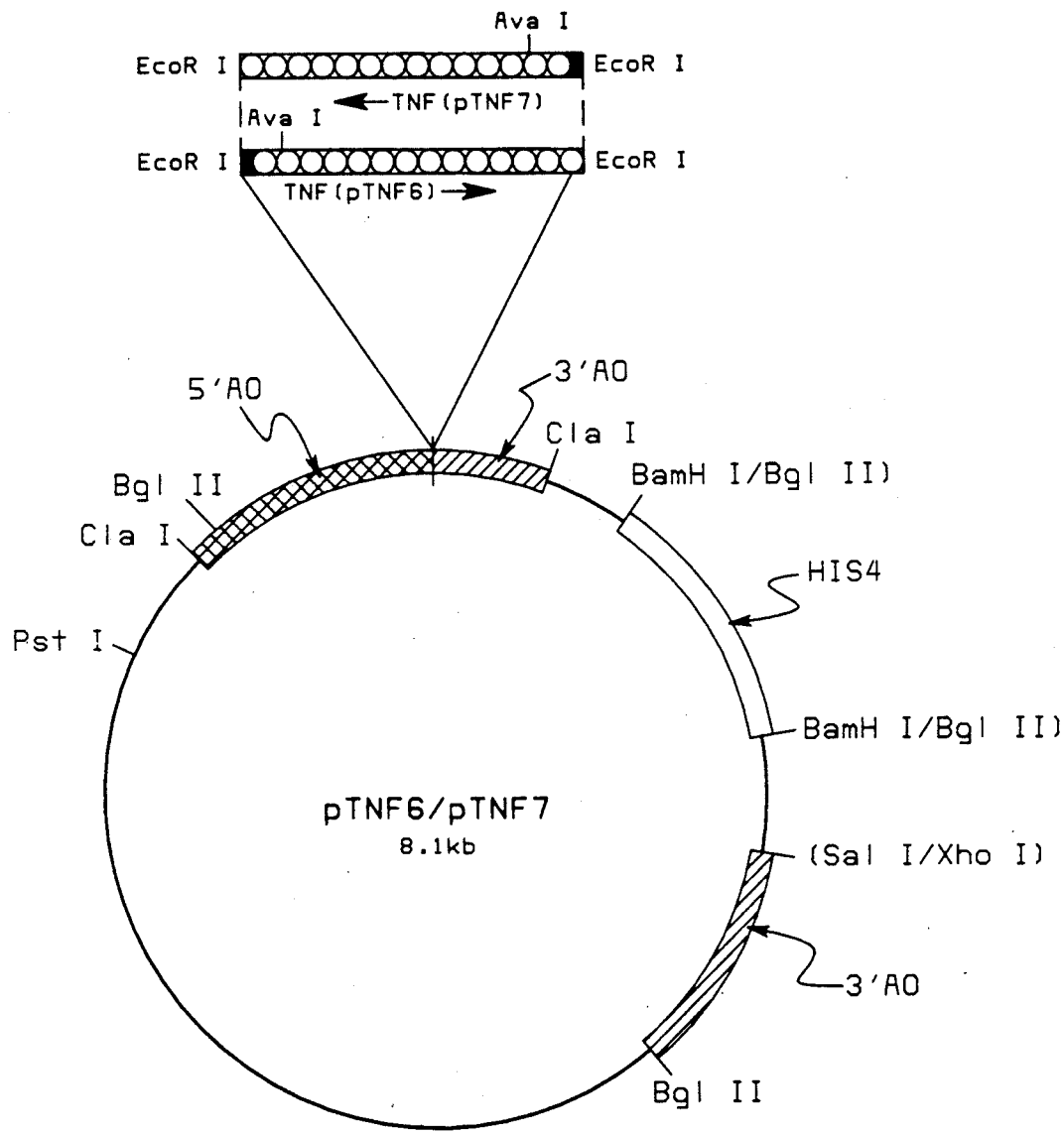
FIG. 7 is a diagram representing the essential components of plasmids pTNF6/pTNF7, including the location of major restriction sites.

Following $R_1$ digestion of plasmid pTNF3, the smaller fragment which contains the TNF gene was isolated by gel electrophoresis followed by electroelution. The purified $R_1$ fragment was then ready for insertion into the $R_1$ sites of such *Pichia pastoris*-based expression vectors such as pTHFK-Δ (see FIG. 3), pA0804 (see FIG. 5), and the like. The TNF gene can be inserted into *Pichia pastoris*-based expression vectors in either orientation. Thus, for example, insertion of the TNF gene into plasmid pTHFK-Δ gives TNF-encoding plasmids pTNF4 and pTNF5 (see FIG. 6), while insertion of the TNF gene into plasmid pA0804 gives TNF-encoding plasmids pTNF6 and pTNF7 (see FIG. 7). The orientation of the TNF gene with respect to the regulatory sequences of the expression vector can be determined by appropriate restriction enzyme analysis. Approximately one half of the resulting TNF-encoding plasmids contain the TNF gene in its correct orientation with respect to the yeast regulatory sequences.

Any yeast regulatory region is suitable for use in the practice of the present invention. The term "regulatory region" as used in this disclosure is intended to include the various functions necessary for controlled gene expression, e.g., promoter regions, upstream activator sequences, catabolite sensitive regions, and the like. Those of skill in the art are aware of numerous regulatory regions which have been characterized and which could be employed in con]unction with the TNF coding region.

Exemplary yeast regulatory regions include the acid phosphatase, galactokinase, alcohol dehydrogenase, cytochrome c, alpha-mating factor and glyceraldehyde 3-phosphate dehydrogenase regulatory regions isolated from *Saccharomyces cerevisiae*; the primary alcohol idase (AOX1), dihydroxyacetone synthase (DAS1) and p40 regulatory regions isolated from *Pichia pastoris*; the *Pichia pastoris* HIS4 regulatory region; and the like Presently preferred regulatory regions employed in the practice of the present invent]-on are characterized by their ability to respond to media-containing:

(1) methanol, (2) non-catabolite repressing carbon sources such as, for example, glycerol, galactose, acetate, and the like, (3) catabolite repressing carbon sources, such as, for example, glucose, ethanol, fructose, and the like, followed by carbon source starvation.

Figure 8:
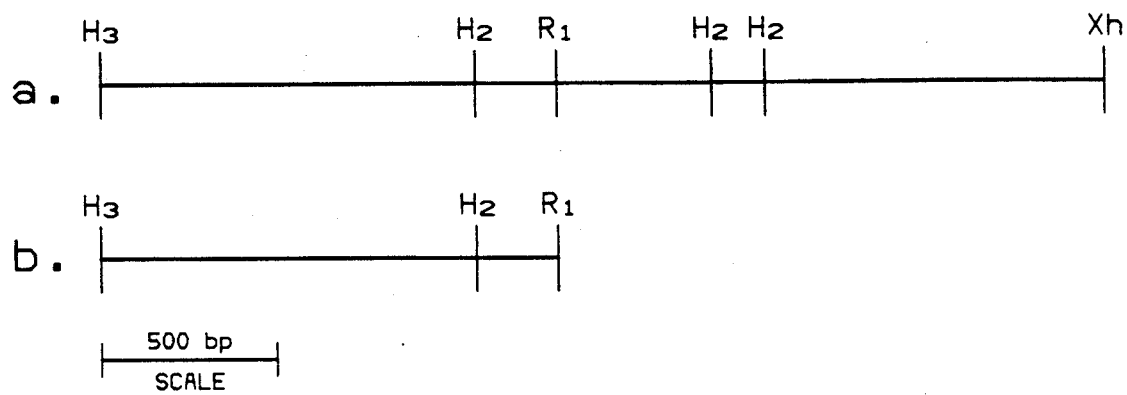
FIG. 8 is a restriction map of the primary *Pichia pastoris* dihydroxyacetone synthease (DAS1) gene regulatory region.
Figure 9:
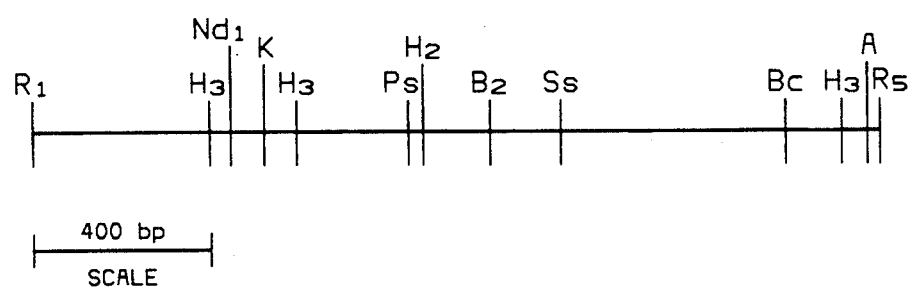
FIG. 9 is a restriction map of the primary *Pichia pastoris* alcohol oxidase (AOX1) gene regulatory region.
Figure 10:
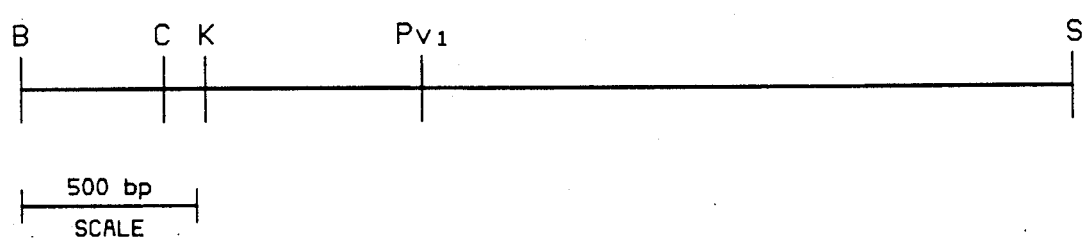
FIG. 10 is a restriction map of the *Pichia pastoris* p40 gene regulatory region.
Figure 13:
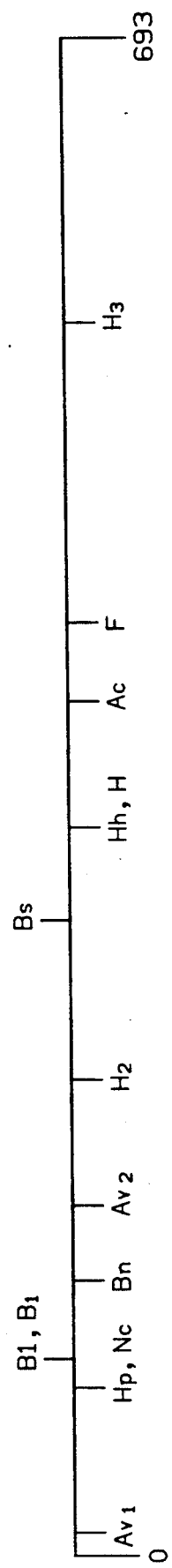
FIG. 13 is a restriction map of the human TNF cDNA.

Examples of these presently preferred regulatory regions are depicted by the restriction maps set forth in FIGS. 8, 9 and 10. The regulatory region depicted in FIG. 8 is derived from the primary dihydroxyacetone synthase (DAS1) gene of *Pichia pastoris*. The regulatory region depicted in FIG. 9 is derived from the primary alcohol oxidase (AOX1) gene of *Pichia pastoris* (*Pichia*

*pastoris* has two alcohol oxidase genes, referred to hereinafter as AOX1 and AOX2). The regulatory region depicted in FIG. 10 is derived from the p40 gene of *Pichia pastoris*. Those of skill in the art recognize that other regulatory regions having the above-described properties can be isolated from methylotrophic yeasts, such as for example, *Pichia pastoris*. Such additional regulatory regions having regulatory properties similar to the properties of the above-described regulatory regions are also within contemplation of the present invention.

The ligation of any of the above described regulatory regions with the human tumor necrosis factor gene is readily accomplished by those of skill in the art by application of known techniques.

The regulatory region-structural gene constructs of the present invention can be supplied to organisms for amplification, reproduction and expression in a variety of ways. For example, the initial ligation mixture can be transformed first into an *E. coli* host for amplification and selection, or the ligation mixture can be transformed directly into a yeast host.

Yeast transformants containing the desired TNF encoding constructs can be selected by appropriate screening of transformed yeast cultures. Assays can then be performed to verify the presence of TNF encoding sequences in the selected transformants. (Assays employed are described in Example V.)

For autonomous replication of the gene constructs in yeast, it is useful to employ an autonomous replication sequence (ARS) element as part of transforming DNA. Examples include PARS1 and PARS2 derived from *Pichia pastoris* as shown in FIGS. 11 and 12, respectively.

Where integrative transformation of the host is instead desired, no ARS element will be employed. A preferred method to achieve integrative transformation involves employing a site directed integration vector which comprises, in serial sequence:
a first insertable DNA fragment,
a TNF coding region,
a selectable marker gene, and
a second insertable DNA fragment.

The first and second insertable DNA fragments are each at least about 200 nucleotides in length and have nucleotide sequences which are homologous to portions of the genomic DNA of species of the genus *Pichia*. The various components of the integrative vector are serially arranged forming a linear fragment of DNA such that the expression cassette and the selectable marker gene are positioned between the 3' end of the first insertable DNA fragment and the 5' end of the second insertable DNA fragment. The first and second insertable DNA fragments are oriented with respect to one another in the serially arranged linear fragment as they are so oriented in the genome of *Pichia pastoris*.

It is necessary to include at least one selectable marker gene in the DNA used to transform the host strain. This facilitates selection and isolation of those organisms which have incorporated the transforming DNA. The marker gene confers a phenotypic trait to the transformed organism which the host did not have, e.g., restoration of the ability to produce a specific amino acid where the untransformed host strain has a defect in the specific amino acid biosynthetic pathway.

Those of skill in the art recognize that additional DNA sequences can also be incorporated into the vectors employed in the practice of the present invention, such as for example, bacterial plasmid DNA, bacteriophage DNA, and the like. Such sequences enable the amplification and maintenance of these vectors in bacterial hosts.

Expression in Transformed Yeast

The above-described plasmids of the present invention have utility in yeast strains which can be transformed. Regulation of TNF expression in yeast by the novel DNA constructs of the present invention can be accomplished by growth of the transformed strains under appropriate inducing or non-inducing conditions. For example, gene expression employing the presently preferred regulatory regions depicted in FIGS. 8, 9 and 10 can be accomplished by subjecting the transformed organisms to carbon source starvation. Carbon source starvation after growth on a variety of both catabolite repressing and non-catabolite repressing carbon sources induces expression of the gene product maintained under the control of the presently preferred regulatory regions of the invention. Another means to achieve expression of the desired gene product in appropriate species of transformed yeast is to grow transformed yeasts on methanol. Yet another means to induce expression of the desired gene product is to grow transformed yeast on media containing non-catabolite repressing carbon sources.

The presently preferred regulatory regions of this invention are useful for TNF expression in all yeast strains, since these regulatory regions have been shown to be functional under a variety of conditions. Thus, yeasts capable of growth on methanol or on non-catabolite repressing carbon sources can be caused to produce TNF directly; while yeasts capable of growth on catabolite repressing carbon sources can be caused to produce TNF by subjecting yeast cells so grown to conditions of carbon source starvation.

Transformed yeast strains which are preferred for use in the process of the present invention employing various regulatory region-coding sequence constructs include members of the genera:
Candida
Kloeckera,
Saccharomyces,
Schizosaccharomyces,
Rhodotorula,
Hansenula,
Torulopsis,
Pichia, and
Kluyveromyces.

Yeasts from these genera are preferred because their safety of handling, growth conditions and the like have been established and are well known to those of skill in the art.

Especially preferred yeast strains for use in the production of TNF in one embodiment of the present invention are those yeast strains which are capable of growth on methanol as carbon and energy source as such hosts are able to well utilize the presently preferred methanol responsive regulatory regions described above. Yeasts known to be capable of growth on methanol include members of the genera:
Candida,
Kloeckera,
Saccharomyces,
Rhodotorula,
Hansenula,
Torulopsis, and Pichia.

Since the presently preferred regulatory regions of the present invention are also induced by growth on non-catabolite repressing carbon sources as well as conditions of carbon source starvation, yeast strains which are capable of growth on such non-methanolic substrates as:
glucose,
acetate,
glycerol,
ethanol,
lactose,
galactose,
fructose,
sucrose,
and the like and mixtures of any two or more thereof are also useful in the practice of the invention. By growing the host organism on a suitable non-catabolite repressible, non-methanolic carbon source such as, for example, glycerol or galactose, or by growing the host organism on a suitable catabolite repressible carbon source such as, for example, ethanol, glucose and fructose, then subjecting the host organism to carbon source starvation conditions, expression of TNF under the control of the presently preferred regulatory regions of the invention can be achieved.

An especially preferred host yeast strain is the mutant *Pichia pastoris* GTS115, which is a mutant defective in the ability to produce histidine. GTS115 has been designated as having the mutant genotype his4, as a result of the defect in the histidine pathway affecting the histidinol dehydrogenase-encoding gene. GTS115 is derived from *Pichia pastoris* NRRL Y-11430 and has been deposited with the Northern Regional Research Center of the United States Department of Agriculture in Peoria, Ill., and has been assigned the accession number NRRL Y-15851. This particular host is useful because it is an auxotrophic mutant deficient in the histidine pathway. Transformation of this host with a vector containing, among other DNA sequences, sequences encoding the HIS4 gene function, allows ready selection of transformed hosts.

Another preferred yeast strain for use in the practice of the present invention is the mutant *Pichia pastoris* GS190, which is a mutant defective in the arginine pathway affecting the argininosuccinate lyase encoding gene. GS190 is derived from *Pichia pastoris* NRRL Y-11430, and has been deposited with the Northern Regional Research Center of the United States Department of Agriculture in Peoria, Ill., and has been assigned the accession number NRRL Y-18014.

Yet another preferred host yeast strain is the double auxotrophic mutant PPF1, which is a mutant defective in both the histidine and arginine pathways. PPF1 is defective in both the histidine pathway affecting the histidinol dehydrogenase encoding gene and the arginine pathway affecting the argininosuccinate lyase encoding gene. PPF1 has been deposited with the Northern Regional Research Center of the United States Department of Agriculture in Peoria, Illinois, and has been assigned the accession number NRRL Y-18017.

*Escherichia coli* is also a suitable host for the manipulation of the plasmids of the present invention. Those of skill in the art recognize that many strains of *E. coli* are readily available and are suitable hosts.

*Pichia pastoris* Transformation Procedure

The experimental procedures for the transformation of *Pichia pastoris* have been previously described, and are presented in greater detail below (Example I).

*Pichia pastoris* can be transformed by enzymatic digestion of the cell walls to give spheroplasts; the spheroplasts are then mixed with the transforming DNA and incubated in the presence of calcium ions and polyethylene glycol, then regenerated in selective growth medium deficient in the gene product on which the host strain cannot grow. The transforming DNA includes the gene which codes for the gene product in which the host strain is deficient, thus only transformed cells survive on the selective growth medium employed.

The desired product, human tumor necrosis factor is produced by growth of transformed cells under conditions under which the regulatory region induces expression of the polypeptide coding region encoding TNF. Those of skill in the art are capable of readily determining such appropriate cultivation conditions without the need for carrying out undue experimentation.

Once the growth of cells and expression of TNF has been carried to acceptable levels, product can be recovered employing a variety of protein recovery means known to those of skill in the art. Exemplary methods include cell disruption by such as vigorous mixing with glass beads, followed by centrifugation to yield a soluble protein extract.

The isolated protein-containing fraction can be assayed in a variety of ways, for example, by polyacrylamide gel electrophoresis of the cellular proteins, by immunoreaction with TNF antibody, biological activity, and the like. Several of these assays are described in greater detail in the Examples.

The invention will now be described in greater detail with reference to the following non-limiting examples.

EXAMPLES

General information pertinent throughout the Examples:

Strains

*Pichia pastoris* GTS115 (his4) [NRRL Y-15851]was the host yeast strain used in these Examples.

*E. coli* K-12 strains CSH7 (lacY rpsL thi) were used for *E. coli* expression of human TNF and *E. coli* DG75' (hsdl, leu-6, lacy, thr-1, supE44, tonA21 lambda [−]) was used for plasmid constructions as well as for propagation of plasmid DNAs.

Plasmids

Plasmids pTNF1, pTHFK-Δ, pBSAGI5I, pA0804, pTNF4/pTNF5 and pTNF6/pTNF7 are illustrated in FIGS. 1, 3, 4, 5, 6 and 7, respectively.

The buffers and solutions employed in the following examples have the compositions given below:

| | |
|---|---|
| 1M Tris buffer | 121.1 g Tris base in 800 mL of H$_2$O; adjust pH to the desired value by adding concentrated (35%) aqueous HCl; allow solution to cool to room temperature before final pH adjustment, dilute to a final volume of 1L. |
| TE buffer | 1.0 mM EDTA in 0.01 M (pH 7.4) Tris buffer |
| SDS Gel Loading Buffer | 62.5 mM Tris-HCl (pH 6.8) 2% SDS 10% glycerol |

|  |  |
|---|---|
|  | 100 mM dithiothreitol |
|  | 0.001% bromphenol blue |
| SED | 1 M Sorbitol |
|  | 25 mM EDTA |
|  | 50 mM DTT |
|  | adjust to pH 8 |
| SCE Buffer | 1 M Sorbitol |
|  | 10 mM Sodium citrate |
|  | 1 mM EDTA |
|  | pH to 5.8 with HCl |
| CaS | 1 M Sorbitol |
|  | 10 mM CaCl$_2$ |
|  | 10 mM Tris-HCl (pH 7.5) |
|  | filter sterilize |
| PEG Solution | 20% polyethylene glycol-3350 |
|  | 10mM CaCl$_2$ |
|  | 10mM Tris-HCl (pH 7.4) |
|  | filter sterilize |
| SOS | 1 M Sorbitol |
|  | 0.3x YPD medium |
|  | 10 mM CaCl$_2$ |

Media

*E. coli* transformants were grown in LB medium with 100 µg/mL ampicillin.

*Pichia pastoris* shake flask cultures were grown in MD, MGY or MM media, and fermentor cultures were grown in IM3 media with YTM4 trace minerals. Carbon sources were 2.0% glucose, 1.0% glycerol, or 0.5% methanol.

All of the following media recipes are expressed in terms of quantity per liter of media:

2xYT—Yeast extract (10 g), tryptone (16 g), NaCl (5 g).
YPD—Yeast extract (10 g), peptone (20 g) and dextrose (10 g).
LB—Yeast extract (5 g), tryptone (10 g), NaCl (10 g) and adjusted to pH 7.5 with NaOH.
LBAp—LB+100 mg ampicillin.
MD—Yeast nitrogen base (YNB, 13.4 g), biotin (400 µg) and dextrose (10 g).
MD(L)—YNB (13.4 g), biotin (400 µg) and dextrose (1.0 g).
MDH—MD+histidine (400 mg).
MGY—YNB (13.4 g), biotin (400 µg) and glycerol (10 mL).
MM—YNB (13.4 g), biotin (400 µg) and MeOH (5 mL).
KDR—YNB (13.4 g), biotin (400 µg), KCl (44.7 g), dextrose (10 g), agar (10 g), histidine assay mix (2 g) and amino acid mixture (50 mg each of the following amino acids: glutamine, methionine, lysine, leucine and isoleucine).
KDHR—KDR+histidine (400 mg).

| FM-21 Salts Medium |  |
|---|---|
| H$_3$PO$_4$(85%) | 3.5 mL |
| CaSO$_4$.2H$_2$O | 0.15 g |
| K$_2$SO$_4$ | 2.38 g |
| MgSO$_4$.7H$_2$O | 1.95 g |
| KOH | 0.65 g |
| FeSO$_4$.7H$_2$O | 0.065 g |
| CuSO$_4$.5H$_2$O | 0.006 g |
| ZnSO$_4$.7H$_2$O | 0.020 g |
| MnSO$_4$.H$_2$O | 0.003 g |
| Biotin | 0.000041 g |
|  | 1 L water |
| IM3 Salts Medium |  |
| KH$_2$PO$_4$ | 15.0 g |
| K$_2$HPO$_4$ | 1.0 g |
| MgSO$_4$.7H$_2$O | 0.50 g |
| CaSO$_4$.2H$_2$O | 0.04 g |
| (NH$_4$)$_2$SO$_4$ | 3.00 g |
| Biotin | 0.00005 g |
| pH to 5.4 |  |
|  | 1 L water |
| YTM-4 Trace Minerals Concentrate |  |
| FeSO$_4$.7H$_2$O | 65.0 g |
| CuSO$_4$.5H$_2$O | 6.0 g |
| ZnSO$_4$.7H$_2$O | 20.0 g |
| MnSO$_4$.H$_2$O | 3.0 g |
|  | 1 L water |
| Add 250 µL/liter of Media |  |

EXAMPLE I

Transformation Procedure

I. *Pichia Pastoris*

A. Cell Growth

Inoculate a colony of *Pichia pastoris* GTS115 (NRRL Y-15851) into about 10 mL of YPD medium and shake culture at 30° C. for 12-20 hours.

2. Inoculate 100 mL of YPD medium with seed culture to give an OD$_{600}$ of about 0.001. Shake at 30° C. for about 12-20 hours.

3. Harvest culture when OD$_{600}$ is about 0.2-0.3 (after approximately 16-20 hours) by centrifugation at 1500 g for 5 minutes.

B. Preparation of Spheroplasts

1. Wash cells once in 10 mL of sterile water. (All centrifugations for steps 1-5 are at 1500 g for 5 minutes.)
2. Wash cells once in 10 mL of freshly prepared SED.
3. Wash cells once in 10 mL of sterile 1 M Sorbitol.
4. Resuspend cells in 10 mL SCE buffer.
5 Add 7.5 µL of 3 mg/mL Zymolyase 100,000 (Miles Laboratories). Incubate cells at 30° C. for about 10 minutes.
6. Wash spheroplasts once in 10 mL of sterile 1 M Sorbitol by centrifugation at 1000 g for 5-10 minutes. (The time and speed for centrifugation may vary; centrifuge enough to pellet spheroplasts but not so much that they rupture from the force.)
7. Wash cells once in 10 mL of sterile CaS.
8. Resuspend cells in total of 1.0 mL of CaS.

C. Transformation

1. Add DNA samples (up to 20 µL volume) to 12×75 mm sterile polypropylene tubes. (DNA should be in a suitable buffer, such as TE buffer; for maximum transformation frequencies with small amounts of DNA, it is advisable to add about 1 µL of 5 mg/mL sonicated *E. colui* DNA to each sample.)
2. Add 100 µL of spheroplasts to each DNA sample and incubate at room temperature for about 20 minutes.
3. Add 1 mL of PEG solution to each sample and incubate at room temperature for about 15 minutes.

D. Regeneration of Spheroplasts

1. Plate Transformation Samples

Pour bottom agar layer of 10 mL Regeneration Agar per plate at least 30 minutes before transformation samples are ready. Distribute 10 mL aliquots of regeneration agar KDR or KDHR to tubes in a 45-50° C. bath during the period that transformation samples are in SOS. Add 50, 250 or 700 µL aliquots of the transformed sample to 10 mL aliquots of melted regeneration agar held at 45-50° C. and pour each onto plates containing a solid 10 mL bottom agar layer of regeneration agar.

2. Incubate plates at 30° C. for 3-5 days. II. *E. coli*

The method of Dagert and Ehrlich (Gene 6, 23 (1979)) was used to transform all strains of E. coli.

EXAMPLE II

Contruction of Pichia pastoris TNF Expression Vectors

In pTNF1, the TNF gene is present on a $B_2$-$Rl_1$ fragment. To insert the TNF gene into the $R_1$ site of Pichia pastoris expression vectors pTHFK-66 (FIG. 3) or pA0804 (FIG. 4), the $B_2$ site had to be converted to an $R_1$ site. This was accomplished by using the strategy schematically depicted in FIG. 2. pTNF1 was digested with $B_2$ to obtain two fragments. The larger fragment contains the TNF gene and also the ori and bla functions. The larger $B_2$ fragment was ligated back to itself. This intermediate plasmid was called pTNF2.

pTNF2 was cleaved with $B_2$ and a dimer of the B-$Av_2$ linker containing an internal $R_1$ was ligated into the $B_2$ site to obtain pTNF3. Such a ligation was possible because B and $B_2$ share the same four nucleotide sequence at the middle of their recognition sites. In a self ligation experiment, it was previously found that the $Av_2$ end of the B-$Av_2$ oligomer was able to ligate with the $Av_2$ end of another linker molecule in spite of one mismatched base pair.

Plasmid pTNF3 was then digested with $R_1$, and the smaller $R_1$ fragment containing the TNF gene was isolated by electroelution following electrophoretic fractionation of the fragments on an agarose gel. The purified $R_1$ fragment was inserted into vectors pTHFK-$\Delta$ and pA0804 at their $R_1$ sites.

Figure 3:
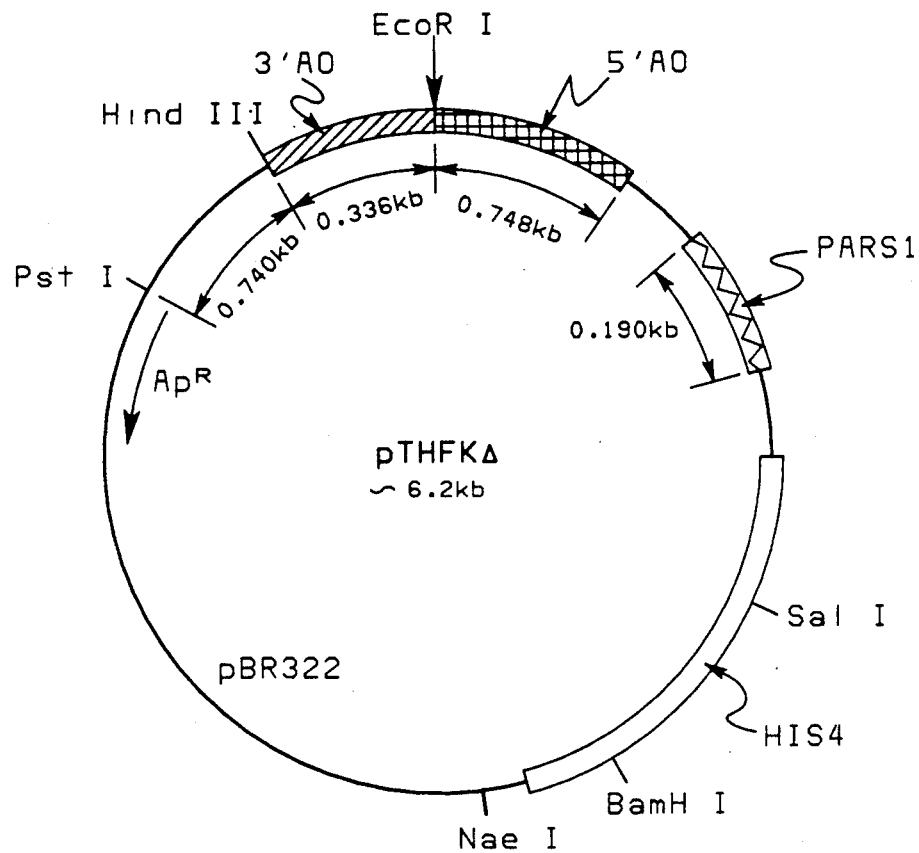
FIG. 3 is a diagram representing the essential components of plasmid pTHFK-Δ, including the location of major restriction sites.
Figure 4:
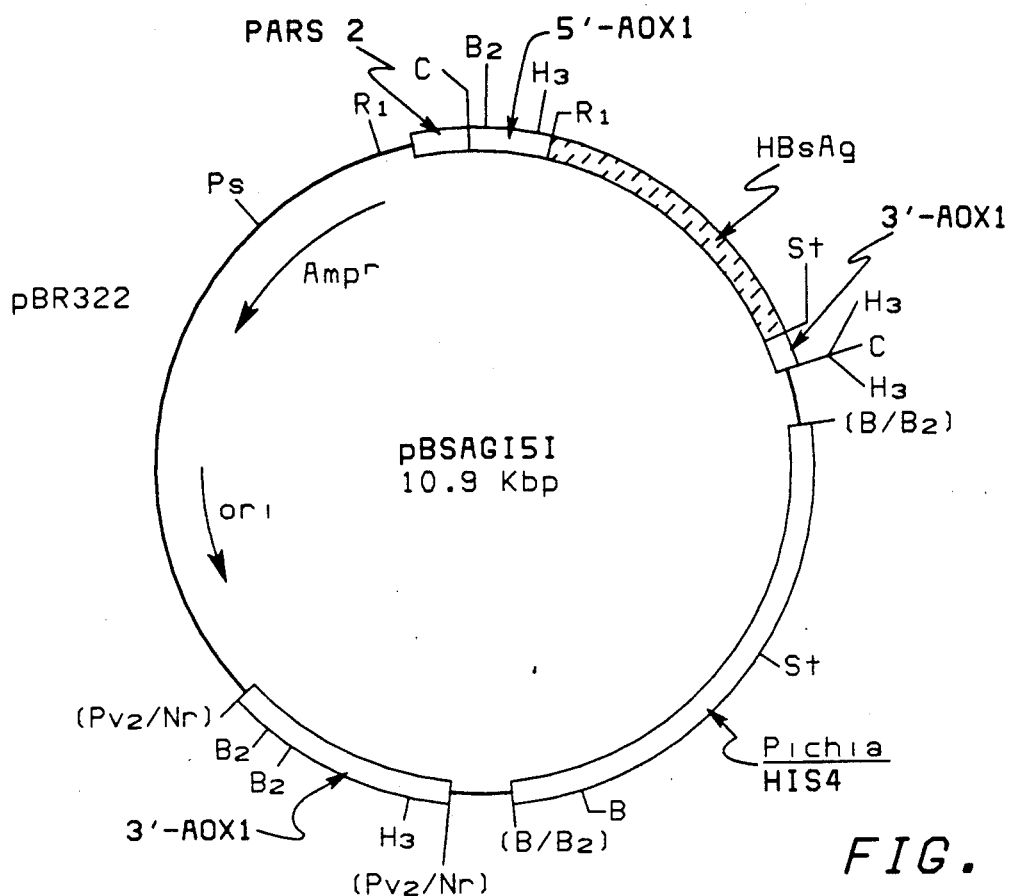
FIG. 4 is a diagram representing the essential components of plasmid pBSAGI5I, including the location of major restriction sites.

Plasmid pTHFK-$\Delta$, illustrated in FIG. 3, was prepared from plasmid pTHBS3V as follows. Plasmid pTHBS3V contains the Pichia pastoris, HIS4, PARS1 and 5'-AOX1 sequences, which can be obtained from plasmid pSAOH5 (which is available in an E. coli host from the Northern Regional Research Center of the United States Department of Agriculture, Peoria, Ill., with the accession number NRRL B-15862), as well as Pichia pastoris 3'-AOX1 sequences, which can be obtained from plasmid pPG4.0 (which is available in an E. coli host from the USDA with accession number NRRL B-15868. The 3.6 Kbp Nr-Ps pBR322 portion of pTHBS3V was replaced with a 1.5 Kbp Nr-Ps fragment derived from a pBR322-based plasmid which is devoid of poison sequences (i.e., the sequence between nucleotides 1,100 and 2,485 of pBR322 were deleted) to produce plasmid pTHBS-3VFK. This plasmid was digested with the restriction enzyme Na, then allowed to self-ligate, producing plasmid pTHFK-$\Delta$. Thus, in pTHFK-$\Delta$, both the E. coli poison sequences and the S site from pBR322 have been deleted.

Plasmid pA0804 was prepared from plasmids pBSAGI5I (shown in FIG. 4, and available in an E. coli host from the Northern Regional Research Center of the United States Department of Agriculture, Peoria, Ill., with the accession number NRRL B-18021), pYJ8 (available in an E. coli host from the Northern Regional Research Center of the United States Department of Agriculture, Peoria, Ill., with the accession number NRRL B-15889), and pBR322 as follows. First, the unique $R_1$ site of pBR322 was eliminated by cutting with $R_1$, filling in the staggered ends using the Klenow fragment of DNA polymerase, then religating. This plasmid is referred to as pBR322 ($R_1^-$). The unique $Pv_2$ site of the plasmid pBR322 ($R_1^-$) was then converted into a $B_2$ site by first cutting with $Pv_2$, then ligating with a synthetic oligonucleotide adapter having the $B_2$ recognition sequence. This plasmid is referred to as pBR322 ($R_1^-$, $Pv_2^{-:B_2}$).

The resulting plasmid pBR322 ($R_1^-$, $Pv_2^-$-$B_2$) was opened with B, and religated with a $B_2$ fragment from pYJ8, which $B_2$ fragment contained the pastoris HIS4-gene. This plasmid is referred to as pBR322 ($R_1^-$, $PV_2^{-:B_2}$HIS4).

Plasmid pBR322 ($R_1^-$, $Pv_2^-$:$B_2$HIS4) was then opened with C, into which was inserted the smaller of the two C fragments obtained from pBSAGI5I (see FIG. 4), which C fragment contains 5'-AOX1 and 3'-AOX1 regulatory sequences from P. pastoris, as well as hepatitis B surface antigen (HBsAg) coding sequences. This plasmid is referred to as pBR322 ($R_1^-$, $Pv_2^-$:$B_2$ HIS4 AOX HBsAg). The latter plasmid was then treated to convert the unique St site within the pBSAGI5I-derived C fragment into an $R_1$ site. This was accomplished by cutting the plasmid with St, then ligating with a synthetic oligonucleotide adapter having the $R_1$ recognition sequence. This plasmid is referred to as pBR322 ($R_1^-$, $Pv_2^{-:B_2}$ HIS4 AOX HBsAg:St$^-$, $R_1^+$).

Finally, the desired plasmid, pA0804, was obtained by deleting the $R_1$ fragment (which contains the HBsAg coding sequences) from plasmid pBR322 ($R_1^-$,$Pv_2^{-:B_2}$ HIS4 AOX HBsAg:St$^-$, $R_1^+$). This was accomplished merely by digestion of the latter plasmid with the restriction enzyme $R_1$ and then religation. The TNF gene was inserted in the vectors pTHFK-$\Delta$ and pA0804 in either orientation. The orientation of TNF gene with respect to the AOX1 promoter was determined by Ps-Av digestion. Thus, in plasmids pTNF4 and pTNF6, the gene is in the correct orientation to be read off the AOX1 promoter. Plasmids pTNF4 and pTNF6, carried in an E. coli host, have been deposited with the Northern Regional Research Center in Peoria, Ill. to ensure access by the public upon issuance of this application as a patent. The deposited strains have been assigned the accession numbers NRRL B-18115 and NRRL B-18114, respectively. In pTNF5 and pTNF7, the gene is in the opposite orientation.

EXAMPLE III

Induction of TNF Expression in E. coli

E. coli strain CSH7/pTNF1 was grown to saturation in LBAp at 30° C. Under these conditions, the $\lambda P_L$ promoter is repressed. To induce TNF expression, the above saturated culture was diluted to an $A_{600}$ ~2.0 into 2xYT medium and incubated for 1½–4 hours at 42° C. At the end of 4 hours, the $A_{600}$ was ~5.0.

Preparation of E. coli Cell Lysate

SDS Lysis: E. coli cells were suspended at an $A_{600}$ ~50 in loading dye mix (1% SDS, 5% $\beta$-mercaptoethanol, 10% glycerol, 10 mM EDTA, 0.025% bromophenol blue) and incubated for five minutes in a boiling water bath. About 5–10 $\mu$L aliquots of the clear lysate were subjected to revealed SDS-PAGE, which revealed a prominent protein band corresponding to TNF in cells induced for TNF expression.

Lysozyme Lysis: E. coli cells were suspended in lysozyme lysis medium (50 mM Tris pH, 30 mM NaCl, 1 mg/mL lysozyme and 1 mM phenylmethylsulfonyl fluoride (PMSF) at an $A_{600}$ ~50 and incubated at 4° C. for 30 minutes. Following lysozyme treatment, the sample was taken through three freeze-thaw cycles and centrifuged in a microfuge for 10 minutes or at 15,000 rpm for 10 minutes in a Sorvall equipped with a SM24 or SA600 rotor. The clear supernatant solution was separated from the pellet and stored at −20° C. Aliquots of 10–20 μL were subjected to SDS-PAGE.

EXAMPLE IV

Yeast Expression of TNF, Growth Conditions

Expression of TNF in *Pichia pastoris* Shake Flask Cultures

*Pichia pastoris* GTS115/pTNF4-1 transformants were grown to saturation in 10 mL of MD or MGY media at 30° C. For induction of TNF synthesis, cells were diluted into 10 mL MM at an $A_{600}$ ~0.1 and grown for four days. At this time, $A_{600}$ was ~8.0 In the case of AOX1 disrupted *Pichia pastoris* transformants, cells from MGY were harvested, washed once with MM and resuspended in MM at an $A_{600} = (A_{600}=2-4)$ and incubated at 30° C. for four days. During this period, the $A_{600}$ for various samples was in the range of about 2 to 8.

Production Studies in the Fermentor

The production of TNF was examined in two continuous culture run and two batch-type fermentation runs. Each run was performed using a 5-liter New Brunswick Scientific fermentor equipped with monitors and controls for pH, dissolved oxygen (D.O.), agitator speed, temperature, air flow and oxygen flow. Temperature was held at 30° C. Cell yields were determined from washed cell dry weights.

Inocula for the fermentor runs were grown in 250 mL Erlenmeyer flasks containing 100 mL of MGY with 1% w/v glycerol as sole source of carbon and energy. The fermentor cultures grown in the batch mode were propagated with 2% w/v glycerol-IM-3 media until the available glycerol was exhausted. Continuous cultures were established using 10% w/v glycerol-FM21 salts feed or 20% w/v glycerol-FM21 salts feed until steady-state conditions were achieved. Once baseline control samples were taken, methanol was added to the culture as either a 15% v/v methanol-salts feed for the culture capable of growth on methanol, a 5% w/v glycerol-1% v/v methanol-FM21 salt feed for a continuous run on a mixed substrate, or as a discontinuous series of methanol additions for those cultures not exhibiting growth on methanol.

EXAMPLE V

Quantification of Yeast Produced TNF

Preparation of *Pichia pastoris* Cell Lysate for TNF Assays

*Pichia pastoris* cells were washed once in the breaking buffer (50 mM sodium phosphate, pH 7.4, 5% glycerol, 1 mM PMSF) and suspended with fresh breaking buffer at an $A_{600}=50-100$ (25–50 g/liter dry cell weight). An equal volume of acid washed glass beads (450–500μ) was added. The mixture was vortexed for a total of four minutes, 30 seconds each time, followed by 30 seconds on ice. The sample was then centrifuged in a microfuge for 10 minutes or at 10,000 rpm for 10 minutes in a Sorvall equipped with a SM24 or SA600 rotor. The clear supernatant solution was siphoned out into a fresh tube and stored at −20° C. Alternatively, *Pichia pastoris* cells at 50–100 g/liter dry cell weight ($A_{600}=100-200$) were directly mixed with an equal volume of glass beads and the cell free extract prepared as before. By either method, the cell free lysate obtained contained about 5–20 mg/mL protein as determined by the method of Lowry et al. In cells expressing TNF, about 5–10 μL of the cell free lysate was sufficient to see a prominent protein band corresponding to TNF by SDS-PAGE.

Quantification of TNF in Cell Extracts

In cell extracts containing significant amounts of TNF, as can be seen as a prominent band of 17,000 molecular weight, the percent TNF present was determined by densitometer (Joycee Loebl microdensitometer) tracing of the Coomassie stained proteins separated by SDS-PAGE. The biological activity of TNF in cell extracts was determined at Wadley Institutes of Molecular Medicine, Dallas, Texas.

EXAMPLE VI

Yeast Production of TNF

Expression of TNF in *Pichia pastoris* GTS115/pTNF4

GTS115 strains transformed with plasmids pTNF4 and, for negative control pTNF5 were grown in 10 mL cultures on MM or MD. Two independent transformants were examined in each case. On MM, the AOX1 promoter is derepressed/induced, whereas in MD, it is repressed. The growth rate of the pTNF4 and pTNF5 transformants on MD and MM were comparable to that of GTS115/pTHFK-Δ. Cell free extracts prepared from the various transformants were analyzed by SDS-PAGE for the presence of TNF. The TNF band was detected only in extract from GTS115/pTNF4-1 and GTS115/pTNF4-2 grown on MM. The amount of TNF produced under these conditions (1 g/L dry cell weight grown on MM for 66 hours) was approximately 1 mg/L. One of the TNF producing transformants, GTS115/pTNF4-1, was grown to a cell density of 46 g/L in a 5-liter chemostat. This transformant performed well with wild type growth characteristics using glycerol or methanol as sole source of carbon and energy. It was during growth on 10% w/v glycerol that the washed cell dry weight of 46 g/L was obtained. Switching the nutrient feed from 10% glycerol to 15 v/v methanol-FM21 salts was accomplished with no intervening starvation period. Once steady-state growth on methanol was stabilized, a dilution rate of 0.067 $hr^{-1}$ (15 hours retention time) was maintained until the end of the continuous run. Yield obtained with methanol as growth substrate was 40%, a value identical to that seen with the wild type *Pichia pastoris* strain under similar growth conditions. Samples were withdrawn at various time intervals and analyzed for TNF production by SDS-PAGE and for activity (Table 1).

TABLE I

| Transformant and Growth Conditions | TNF Production by *P. pastoris* GTS115/pTNF4-1 and *E. coli* CSH7/pTNF1 | | | | TNF Activity U/mg of Soluble Protein |
|---|---|---|---|---|---|
| | Carbon Source | Cell Density (Dry Cell Weight/L) | Dilution Rate, $h^{-1}$ | Hours | |
| GTS115/pTNF4-1 | Glycerol | 46 g/L | 0.086 | −2 h* | $6.3 \times 10^3$ |

TABLE I-continued

TNF Production by P. pastoris GTS115/pTNF4-1 and E. coli CSH7/pTNF1

| Transformant and Growth Conditions | Carbon Source | Cell Density (Dry Cell Weight/L) | Dilution Rate, $h^{-1}$ | Hours | TNF Activity U/mg of Soluble Protein |
|---|---|---|---|---|---|
| Fermentor Run (Continuous Culture) | | | | | |
| | Methanol | 46 g/L | 0.043 | 5 h | $9.1 \times 10^4$ |
| | Methanol | 46 g/L | 0.067 | 76 h | $9.8 \times 10^4$ |
| | Methanol | 46 g/L | 0.067 | 168 h | $6.0 \times 10^4$ |
| GTS115/pTNF4-1 Shake Flask on MM Medium | Methanol | ~1 g/L | NA | 72 h | $8.6 \times 10^4$ |
| CSH7/pTNF1 Shake Flask on 2xYT Medium | — | ~1 g/L | NA | 4 h (at 42° C.) | $6.5 \times 10^5$ |

*Refers to two hours prior to switching to methanol.
NA - Not applicable.

Based on the results of SDS-PAGE analysis and the results summarized in Table I, it can be concluded that TNF production was induced rapidly upon switching to methanol and proceeded fairly stably for at least 168 hours. TNF produced in *Pichia pastoris* has biological specific activity at least as high as, or perhaps more than, that of *E. coli* TNF. Based on the amount of TNF estimated by visual comparison of the staining intensity, the percent of TNF produced in *Pichia pastoris* in this experiment represented about 0.5-1% of the total soluble protein. Also, the amount of TNF produced (percent of total soluble protein) in shake flask culture (1 g/L) was similar to that produced in the high-cell-density chemostat (46 g/L), suggesting that there was no loss of efficiency of TNF production in the scale-up. Electrophoretic analysis of DNA isolated from fermentor samples indicated that some autonomous plasmid pTNF4 was present in the glycerol grown cells. No free plasmid DNA was detected by ethidium bromide staining in total DNA from methanol grown cells. This suggests plasmid integration during growth on methanol. As seen in Table II (presented below), the values for percent stability of the His+ marker support the speculation that plasmid pTNF4 is stably integrated (at least the HIS4 marker of the plasmid) in methanol grown cells. Since both the 5' AOX1 and 3' AOX1 regions are present in the TNF expression plasmid pTNF4, there was some possibility that the plasmid integration in some cells could result in disruption of the AOX1 gene. This possibility was tested by screening 250 His+ colonies for growth on methanol (Table II). Every one of the His+ colonies grew well on MM, suggesting that in these colonies plasmid integration was not accompanied by disruption of the endogenous AOX1.

TABLE II

Stability of His+ and MeOH+ Phenotypes in GTS115/pTNF4-1 Grown in the Fermentor

| Sample | % Stability of His+ Marker | % Stability of MeOH+ Phenotype |
|---|---|---|
| Cells on Glycerol (−2 h Fermentor Sample, see Table I) | 26 | Not Determined |
| Cells on Methanol (168 h Fermentor Sample, see Table I) | 100 | 100 (Number of colonies tested = 250) |

GTS115/pTNF4-1 cells from the fermentor were diluted in water and appropriate dilutions were spread on MDH plates. Colonies that appeared on MDH were replica plated onto MD plates. Percent His+ stability was calculated by comparing the number of colonies that grew on an MD plate to the number on a corresponding MDH plate. Methanol grown cells were 100% stable for the His+ marker, suggesting plasmid integration. Colonies on MDH plates were also replica plated onto MM plates to determine whether plasmid integration was accompanied by deletion of the alcohol oxidase gene (AOX1).

B. Expression of TNF in His+-Methanol Slow Transformants

1. Integrative Transformation of GTS115 to Disrupt AOX1 with AOX1:TNF

Previous work in *pastoris* suggested that disruption of the endogenous AOX1 of *Pichia pastoris* could result in high expression levels of heterologous proteins. Therefore, the expression of the AOX1:TNF expression cassette in AOX1 disrupted GTS115 was examined as follows. GTS115 was transformed with $B_2$ digested pTNF6 (the larger $B_2$ DNA fragment contains the AOX1 replacement cassette). This transformation resulted in the formation of numerous His+ transformants. For comparison, $B_2$ cleaved pA0804 and pBSAGI5I were also used for transformation. The transformation results are summarized in Tables III and IV.

TABLE III

Integrative Transformation of P. pastoris GTS115 with $B_2$ Cleaved Plasmids

| Plasmid (Size in Kb) | Size of $B_2$ Cleaved DNA Fragment Containing HIS4 Gene | Transformation Frequency No. of His+ Transformants/ μg of DNA | No. of MeOH− Transformants (% of His+ Colonies Tested) |
|---|---|---|---|
| pTNF6 (8.1) | 5.8 kb | 14 (20)* | 8.3 |
| pA0804 (7.4) | 5.1 kb | 40 (58) | 5.2 |
| pBSAGI5I | 6.4 kb | 111 (187) | 8.4 |

TABLE III-continued

Integrative Transformation of P. pastoris GTS115 with B2 Cleaved Plasmids

| Plasmid (Size in Kb) | Size of B2 Cleaved DNA Fragment Containing HIS4 Gene | Transformation Frequency No. of His+ Transformants/ μg of DNA | No. of MeOH− Transformants (% of His+ Colonies Tested) |
|---|---|---|---|
| None | — | 0 | 8.4 |

*Values in the parenthesis represent transformation frequency per μg of HIS4 containing DNA fragment.
P. pastoris GTS115 was transformed with 10–20 μg of B2 cleaved plasmids. Prior to transformation, an aliquot of the B2 digested DNA samples were tested for complete cleavage by agarose gel electrophoresis followed by ethidium bromide staining for visualization of DNA fragments. Yeast transformation was carried out as described in Example I. His+ transformants were transferred to MDL plates and replica plated onto MM
plates to test for methanol slow (MeOH−) phenotype.

TABLE IV

Rescreening of His+ MeOH− - GRS115 Transformants

| His+ MeOH−- Transformant | Number of Transformants Tested | Phenotype* on MM Plate (% of Total No. Tested) | | | |
|---|---|---|---|---|---|
| | | N | I | S | N + (I or S) |
| GTS115/pTNF6 | 23 | 4 | 73 | 14 | 9 |
| GTS115/pA0804 | 20 | 10 | 80 | — | 10 |
| GTS115/pBSAGI5I | 24 | 8 | 9 | 63 | 20 |

His+ MeOH− - GTS115 transformants (see Table III) were plated onto MDL and rescreened for MeOH− phenotype by streaking onto MM plates.
*Key:
N = Normal growth on MM
I = Intermediate growth on MM
S = Slow or no growth on MM
N + (I or S) = Mixture of colonies with normal and intermediate or slow growth on MM As seen in Table III, pTNF6 gave considerably lower frequency of His+ transformants compared with pBSAGI5I or pA0804 To screen for *Pichia pastoris* that grew slowly on methanol, colonies on MDL were replica plated onto MM. About 5–8% of the His+ transformants grew slowly on methanol. Methanol slow phenotype is indicative of AOX1 disruption by the transforming DNA. A set of randomly selected methanol slow clones were rescreened to confirm the phenotype. As given in Table IV, most of the colonies from the initial screen were scored as methanol slow in the second screen. However, among the methanol slow colonies, two distinct phenotypes were observed, namely clones that did not grow on MM, referred to as methanol slow (S) and clones that had intermediate growth at the end of four days of incubation at 30° C., referred to as methanol slow (I). Plasmid pBSAGI5I gave a higher percent of methanol slow (S) compared to either pA0804 or pTNF6. In the case of the latter two plasmids, intermediate methanol slow (I) was more predominant. Some colonies were mixtures of methanol normal (N) and methanol slow (I or S) cells due to the presence of mixed populations of methanol normal and methanol slow transformants.

2. Expression of TNF in His+-Methanol Slow Transformants

Six methanol slow isolates of GTS115/pTNF6 were grown in shake flasks to an $A_{600}$ in the range of 3–5 (approximately 1 g/L dry cell weight) in 10 mL MGY and induced for TNF production by switching to MM. After 100 hours on MM, cells were harvested, lysed and the cell free extract was analyzed for TNF by SDS-PAGE. For comparison, extracts from similarly treated GTS115/pA0804 and GTS115/pBSAGI5I were also analyzed. TNF expression levels for each of these transformants are presented in Table V.

TABLE V

Analysis of His+ MeOH− - GTS115/pTNF6 Transformants for Expression of TNF

| Transformant | $A_{600}$ | | TNF |
|---|---|---|---|
| | 0 h | 100 h | (% of Soluble Protein) |
| GTS115/pTNF6-1 | 3.2 | 7.2 | <1% (Low) |
| GTS115/pTNF6-2 | 3.3 | 2.8 | >30% (High) |
| GTS115/pTNF6-3 | 2.0 | 3.8 | ~5% (Intermediate) |
| GTS115/pTNF6-4 | 2.2 | 4.0 | <1% (Low) |
| GTS115/pTNF6-6 | 4.7 | 8.2 | <30% (High) |
| GTS115/pTNF6-6 | 3.3 | 4.9 | ~5% (Intermediate) |
| GTS115/pA0804 | 2.0 | 4.6 | NA |
| GTS115/pBSAGI5I-1 | 3.0 | 7.7 | NA |

His+ MeOH− - GTS115 transformants were grown to an $A_{600}$ = 2-5 in 10 mL of MD. Cells were pelleted, washed once with 10 mL MM, resuspended in 10 mL of fresh MM and the $A_{600}$ value (optical density at 600 nm) determined (0 h value). Cells in MM media were incubated at 30° C. in a shaker bath for 100 h, the $A_{600}$ was measured (100 h value) and cell free extracts were prepared as described in Example V. Aliquots of cell extracts were
subjected to SDS-PAGE and stained with Coomassie Brilliant Blue. Stained protein bands were traced in a densitometer to determine the percent of TNF in the samples.

In all the transformants tested, except for GTS115/pTNF6-2, the cells doubled approximately once during growth on MM for 100 hours. Among the cell free extracts of GTS115/pTNF6-(1 through 6) clones analyzed by SDS-PAGE, clones 2 and 5 contained the highest amounts of TNF. One of these clones, referred to as GTS115/pTNF6-5, has been deposited with the Northern Regional Research Center in Peoria, Illinois, to ensure access by the public upon issuance of this application as a patent, and has been assigned accession number NRRL Y-18116. Clones 1 and 3 had very low levels and clones 3 and 6 had moderate levels of TNF (see Table V). Based on densitometer tracing results, the amount of TNF produced in clones 2 and 5 was estimated to be in the range of about 30% of the soluble protein. These two high TNF producers were examined for TNF production in a fermentor (see below). As expected, no protein band corresponding to TNF was present in GTS115/pA0804-1 and GTS115/pBSAGISI cell extracts.

3. Production of TNF from GTS115/pTNF6-2 in Batch Fermentor

GTS115/pTNF6-2 grew well on glycerol but, as expected, would not grow on methanol. Steady-state growth on 10% w/v glycerol in a chemostat yielded a washed dry cell weight of 57 g/L. Turning off the nutrient feed resulted in an immediate rise in the D.O. levels. After a 30 minute carbon starvation period, 10 mL of methanol was added to the 2000 mL culture. An immediate decrease in both D.O. and pH was noted, which indicated that the cells had the ability to oxidize the added methanol. A total of 100 mL (79 g) of methanol was added to the culture over a period of 143 hours. The ability of the culture to oxidize the methanol was highest during the first 24 hours, which was followed by a slow decline in the oxidation rate. No growth was exhibited by the culture even though nearly all of the added methanol was consumed. Samples were withdrawn from the fermentor prior to addition of methanol and at different time intervals following addition of methanol. Cell free extracts from fermentor cells were analyzed by SDS-PAGE. As in Table VI, the amount of TNF in *Pichia* cell extracts raised rapidly from as low as around 2% on glycerol to 13% within 3 hours on methanol addition and then saturated at around 25% within 48 hours and continued to remain at that level throughout the length of the experiment (142 h).

TABLE VI

Production of TNF by *P. pastoris* GTS115/pTNF6-2 in the Fermentor Batch Culture

| Carbon Source | $D^1$ | $CW^2$ | Hours on Methanol | TNF (% of Soluble Protein) | Units/mg of Soluble Protein |
|---|---|---|---|---|---|
| Glycerol | 0.055 | 57 | $-1^3$ | $ND^4$ | $6 \times 10^4$ |
| Methanol | 0 | — | 3 | 13.1 | $25 \times 10^4$ |
| Methanol | 0 | — | 10.5 | 17.7 | $68 \times 10^4$ |
| Methanol | 0 | — | 24.0 | 17.7 | $60 \times 10^4$ |
| Methanol | 0 | — | 48.0 | 24.7 | $196 \times 10^4$ |
| Methanol | 0 | — | 79.0 | 25.7 | $115 \times 10^4$ |
| Methanol | 0 | — | 100.0 | 24.4 | $210 \times 10^4$ |
| Methanol | 0 | 50 | 142.0 | 23.9 | $190 \times 10^4$ |

$^1$D = Dilution rate
$^2$CW = Washed Cell Dry Weight
$^3$Refers to one hour prior to switching to methanol
$^4$ND = Not determined
Fermentor Conditions:
Temperature = 30° C., pH = 5.0, Volume = 2 liters
Methanol Consumption = 87 mL 4. Production of TNF from GTS115/pTNF6-5 in Batch Fermentor GTS115/pTNF6-5 was grown on 20% w/v glycerol to a steady-state growth yield of 108 g/L dry cell weight. After a 30-minute starvation period, 20 mL of methanol was added to the 2000 mL culture. Similar to the run with GTS115/pTNF6-2, an immediate decrease in both D.O. and pH was noted. A total of 275 mL (217 g) of methanol was added to the culture over a period of 189 hours. Nineteen methanol additions were required over the time period. Nearly all of the methanol was oxidized. Even though GTS115/pTNF6-5 had shown some growth on methanol at 1 g/L cell density in the shake flask, under the conditions of high-cell-density growth in the fermentor, no growth on methanol was observed. As seen in Table VII, the production of TNF in GTS115/pTNF6-5 cells was rapidly induced upon shifting to methanol and appeared to reach saturation values within 48 hours and the TNF level continued to be steady until the end of the run (189 h).

TABLE VII

Production of TNF by *P. pastoris* GTS115/pTNF6-5 in the Fermentor Batch Culture

| Carbon Source | $D^1$ | $CW^2$ | Hours on Methanol | TNF (% of Soluble Protein) | Units/mg of Soluble Protein |
|---|---|---|---|---|---|
| Glycerol | 0.078 | 108 | $-1^3$ | 9.8 | ND |
| Methanol | 0 | — | 23 | 22.1 | $40 \times 10^4$ |
| Methanol | 0 | — | 43 | 28.0 | $120 \times 10^4$ |
| Methanol | 0 | — | 88 | 27.1 | $260 \times 10^4$ |
| Methanol | 0 | — | 136 | 28.6 | $110 \times 10^4$ |
| Methanol | 0 | 85 | 189 | 32.0 | $100 \times 10^4$ |

$^1$D = Dilution rate
$^2$CW = Washed cell dry weight
$^3$Refers to one hour prior to switching to methanol
$^4$ND = Not determined
Fermentor Conditions:
Temperature = 30° C., pH = 5.0, Volume = 2 liters
MeOH Consumption = 274 mL GTS115/pTNF6-5 produces a significantly higher amount of TNF (9%) when grown on glycerol compared to GTS115/pTNF6-2 (2% TNF) grown on glycerol. When grown on methanol the expression level of TNF in GTS115/pTNF6-5 was around 32%. This value is slightly higher than that observed with GTS115/pTNF6-2 grown on methanol.

5. Production of TNF from GTS115/pTNF6-5 During Growth on a Glycerol-methanol Mixture GTS115/pTNF6-5 was grown on 5% w/v glycerol-FM21 salts feed to steady-state conditions. The feed was switched from glycerol to a mixed feed comprising 5% w/v glycerol + 1% v/v methanol with no intervening starvation period. A continuous culture was maintained on the glycerol-methanol mixture for 73 hours. Although GTS115/pTNF6-5 was not capable of growth on methanol as sole source of carbon and energy, it would grow on glycerol and oxidize methanol concomitantly in a chemostate at a dilution rate of 0.05 $hr^{-1}$. As seen in Table VIII, the methanol concentration in the fermentor remained well below 1% v/v throughout the run.

TABLE VIII

Production of TNF by *P. pastoris* GTS115/pTNF6-5 in the Fermentor - Continuous Culture on Methanol + Glycerol

| Carbon Source | Hours on Glycerol + Methanol | Residual Methanol Concentration (% w/v) | % of Soluble Protein | Units/mg of Soluble Protein |
|---|---|---|---|---|
| 5% (w/v) Glycerol | $-4^*$ | 0 | 7.0 | $2.8 \times 10^5$ |
| 5% (w/v) Glycerol + 1% (w/v) Methanol | 18 | 0.1 | 18.9 | $5 \times 10^5$ |
| 5% (w/v) Glycerol + 1% (w/v) Methanol | 26 | 0.08 | 18.5 | $5.8 \times 10^5$ |
| 5% (w/v) Glycerol + 1% (w/v) Methanol | 43 | 0.05 | 18.6 | $6 \times 10^5$ |
| 5% (w/v) Glycerol + | 73 | 0.20 | 16.5 | $5 \times 10^5$ |

TABLE VIII-continued

Production of TNF by *P. pastoris* GTS115/pTNF6-5 in the Fermentor - Continuous Culture on Methanol + Glycerol

| Carbon Source | Hours on Glycerol + Methanol | Residual Methanol Concentration (% w/v) | % of Soluble Protein | Units/mg of Soluble Protein |
|---|---|---|---|---|
| 1% (w/v) Methanol | | | | |

*Refers to four hours prior to switching to glycerol + methanol
Dilution rate = 0.05 $h^{-1}$
Volume = 2 liters
Flow Rate = 100 mL/h
Total flow in 73 hours = 7.3 liters As seen in Table VIII, the amount of TNF in *Pichia pastoris* cell extracts raised rapidly upon shifting to the glycerol-methanol mixture and remained steady throughout the length of the experiment (73 h). The amount of TNF in fermentor cells grown on the glycerol-methanol mixture was around 17% of soluble protein (See Table VIII).

The examples have been provided merely to illustrate the practice of our invention and should not be read so as to limit the scope of our invention or the appended claims in any way. Reasonable variations and modifications, not departing from the essence and spirit of our invention, are contemplated to be within the scope of patent protection desired and sought.

What is claimed is:

1. An essentially pure culture of a strain of the species Pichia pastoris transformed with a plasmid selected from the group consisting of the plasmids pTNF4 and pTNF6.

2. The plasmid pTNF4.

3. The plasmid pTNF6.

4. A process for preparing human tumor necrosis factor which comprises cultivating a yeast strain transformed with the plasmid of claim 2 under conditions under which the regulatory region induces expression of the polypeptide coding region encoding human tumor necrosis factor.

5. A process in accordance with claim 4 further comprising isolating and purifying said human tumor necrosis factor.

6. A process for preparing human tumor necrosis factor which comprises cultivating a yeast strain transformed with the plasmid of claim 3 under conditions under which the regulatory region induces expression of the polypeptide coding region encoding human tumor necrosis factor.

7. A process in accordance with claim 6 further comprising isolating and purifying said human tumor necrosis factor.

* * * * *